United States Patent [19]

Shiokawa et al.

[11] Patent Number: 5,234,930
[45] Date of Patent: Aug. 10, 1993

[54] PYRAZOLOPYRIDINE COMPOUNDS WHICH HAVE USEFUL PHARMACEUTICAL UTILITY

[75] Inventors: Youichi Shiokawa, Ibaraki; Atsushi Akahane, Hyogo; Hirohito Katayama, Nishinomiya; Takafumi Mitsunaga, Ashiya, all of Japan

[73] Assignee: Fujisawa Pharmaceutical Co., Ltd., Osaka, Japan

[21] Appl. No.: 866,215

[22] Filed: Apr. 9, 1992

[30] Foreign Application Priority Data

Apr. 10, 1991 [GB] United Kingdom ................ 9107513

[51] Int. Cl.$^5$ .................. A61K 31/435; C07D 471/04
[52] U.S. Cl. ..................... 514/300; 546/121
[58] Field of Search ......................... 546/121; 514/300

[56] References Cited

U.S. PATENT DOCUMENTS 4,994,453 2/1991 Shiokawa et al. ................... 514/212
5,102,878 4/1992 Shiokawa et al. ................... 514/212

FOREIGN PATENT DOCUMENTS 0299209 1/1989 European Pat. Off. ............ 546/121
0379979 8/1990 European Pat. Off. ............ 546/121

*Primary Examiner*—C. Warren Ivy
*Assistant Examiner*—Zinna N. Davis
*Attorney, Agent, or Firm*—Oblon, Spivak, McClelland, Maier & Neustadt

[57] ABSTRACT

This invention relates to pyrazolopyridine compounds for the treatment of melancholia, heart failure, hypertension, renal insufficiency, renal toxicity, nephrosis, nephritis, edema, obesity, bronchial asthma, gout, hyperuricemia, sudden infant death syndrome, immunosuppression, diabetes, myocardial infarction, thrombosis, obstruction, arteriosclerosis obliterans, thrombophlebitis, cerebral infarction, transient ischemic attack or angina pectoris, said compounds being of the formula

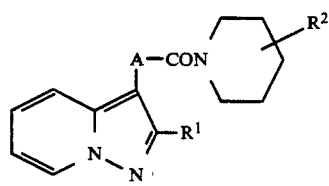

wherein the radicals are defined in the claims.

11 Claims, No Drawings

PYRAZOLOPYRIDINE COMPOUNDS WHICH HAVE USEFUL PHARMACEUTICAL UTILITY

The present invention relates to novel pyrazolopyridine compound and a pharmaceutically acceptable salt thereof.

More particularly, it relates to novel pyrazolopyridine compound and a pharmaceutically acceptable salt thereof, which are adenosine antagonists and posses various pharmaceutical actions such as cognitive enhancing action, analgesic action, locomotor action, antidepressant action, cerebral vasodilating action, diuretic action, cardiotonic action, vasodilating action, the action of increasing the renal blood flow, renal prophylactic effect, improvemental effect of renal function, enhanced lipolysis action, inhibited anaphylactic bronchoconstrictive action, accelerating action of the release of insulin, or the like, and so are useful as psychostimulant, analgesic, antidepressant, ameliorants of cerebral circulation, drug for heart failure, cardiotonic agent, antihypertensive agent, drug for renal insufficiency (renal failure), drug for renal toxicity, renal prophylactic agent, improvement agent of renal function, diuretic, drug for edema, antiobesity, antiasthmatic, bronchodilater, drug for apnea, drug for gout, drug for hyperuricemia, drug for sudden infant death syndrome (SIDS), ameliorants of immunosuppresion action of adenosine, antidiabetic agent, or the like, and further which are inhibitors of platelet aggregation ,so are useful as drug for thrombosis, drug for myocardiac infarction, drug for obstruction, drug for arteriosclerosis obliterans, drug for thrombophlebitis, drug for cerebral infarction, drug for transient ischemic attack, drug for angina pectoris, or the like; to a process for preparation thereof, to a pharmaceutical composition comprising the same, ad to a method for using the same therapeutically in human being and animals for the prevention and/or treatment of melancholia, heart failure, hypertension (e.g. essential hypertension, nephrogenous hypertension, etc), renal insufficiency (renal failure) (e.g. acute renal failure, etc), renal toxicity [e.g. renal toxicity induced by a drug such as cisplatin, gentamicin, FR-900506 (disclosed in EP-0184162), cyclosporins (e.g. cyclosporin A) or the like; glycerol; etc], nephrosis, nephritis, edema (e.g. cardiac edema, nephrotic edema, hepatic edema, idiopathic edema, drug edema, acute angioneurotic edema, hereditary angioneurotic edema, carcinomatous ascites, gestational edema, etc), obesity, bronchial asthma, gout, hyperuricemia, sudden infant death syndrome, immunosuppresion, diabetes, myocardiac infarction, thrombosis (e.g. arterial thrombosis, cerebral thrombosis, etc.), obstruction, arteriosclerosis obliterans, thrombophlebitis, cerebral infarction, transient ischemic attack, angina pectoris or the like.

Accordingly, one object of the present invention is to provide the novel pyrazolopyridine compound and a pharmaceutically acceptable salt thereof, which are useful as stated above.

Another object of the present invention is to provide processes for the preparation of the novel pyrazolopyridine compound or a salt thereof.

A further object of the present invention is to provide a pharmaceutical composition comprising, as an active ingredient, said pyrazolopyridine compound or a pharmaceutically acceptable salt thereof.

Still further object of the present invention is to provide a method for using said pyrazolopyridine compound as aforesaid therapeutic use, which comprises administering said pyrazolopyridine compound to human being or animals.

The novel pyrazolopyridine compound of the present invention can be shown by the following formula (I).

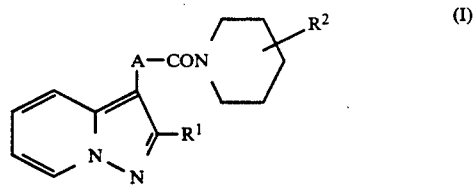

wherein
$R^1$ is aryl,
$R^2$ is acyl(lower)alkyl, and
A is lower alkenylene.

The object compound (I) or a salt thereof of the present invention can be prepared by the following reaction schemes.

Process 1

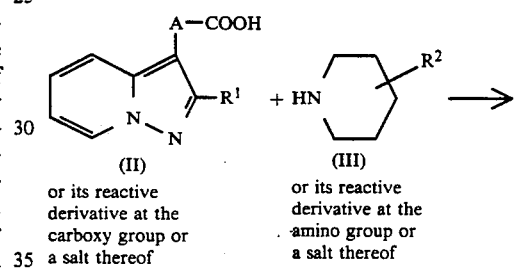

(II)
or its reactive derivative at the carboxy group or a salt thereof (III)
or its reactive derivative at the amino group or a salt thereof

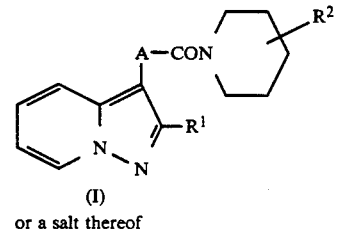

(I)
or a salt thereof

Process 2

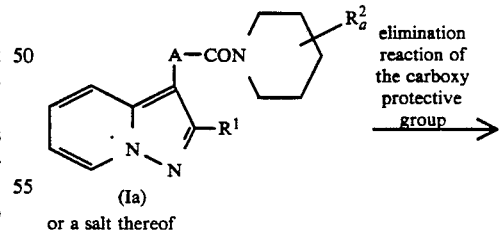

(Ia)
or a salt thereof elimination reaction of the carboxy protective group

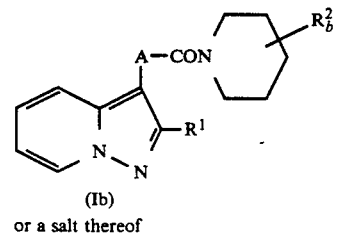

(Ib)
or a salt thereof

Process 3

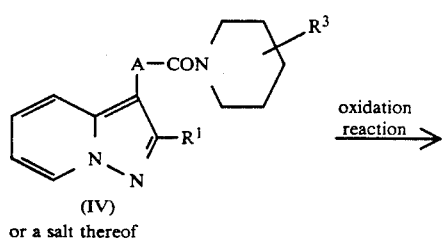

(IV)
or a salt thereof oxidation reaction →

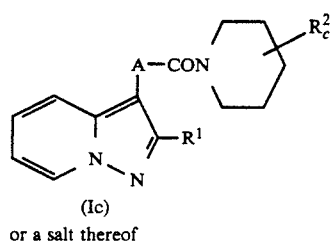

(Ic)
or a salt thereof

Process 4

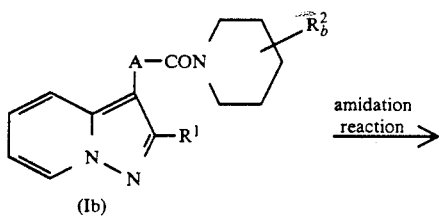

amidation reaction →

(Ib)
or its reactive derivative
at the carboxy group
or a salt thereof

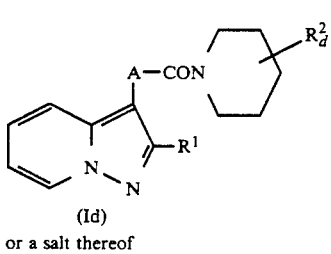

(Id)
or a salt thereof wherein
R$^1$, R$^2$ and A are each as defined above,
R$^2_a$ is protected carboxy(lower)alkyl,
R$^2_b$ is carboxy(lower)alkyl,
R$^2_c$ is formyl(lower)alkyl or carboxy(lower)alkyl,
R$^2_d$ is amidated carboxy(lower)alkyl, and
R$^3$ is hydroxy(lower)alkyl.

It is to be noted that the object compound (I) may include the geometrical isomer(s) due to the double bond(s) and/or the stereo isomer(s) due to the asymmetric carbon atoms(s). In this regard, one isomer can be converted to another according to a conventional manner in this field of the art.

Suitable pharmaceutically acceptable salts of the object compound (I) are conventional ones and include a metal salt such as an alkali metal salt (e.g. sodium salt, potassium salt, etc) and an alkaline earth metal salt (e.g. calcium salt, magnesium salt, etc), an ammonium salt, an organic base salt (e.g. trimethylamine salt, triethylamine salt, pyridine salt, picoline salt, dicyclohexylamine salt, N,N'-dibenzylethylenediamine salt, etc), an organic acid salt (e.g. acetate, trifluoroacetate, maleate, tartrate, fumalate, methanesulfonate, benzenesulfonate, formate, toluenesulfonate, etc), an inorganic acid salt (e.g. hydrochloride, hydrobromide, hydriodide, sulfate, phosphate, etc), a salt with an amino acid (e.g. arginine, aspartic acid, glutamic acid, etc), and the like.

In the above and following descriptions of the present specification, suitable examples and illustrations of the various definitions which the present invention includes within the scope thereof are explained in detail as follows.

The term "lower" is intended to mean 1 to 6 carbon atom(s) unless otherwise indicated.

Suitable "aryl" may include phenyl, naphthyl, indenyl, anthryl and the like, in which the preferred one may be phenyl.

Suitable "lower alkyl" may include straight or branched ones such as methyl, ethyl, propyl, isopropyl, butyl, t-butyl, pentyl, hexyl or the like, in which the preferred one may be (C$_1$-C$_4$)alkyl and the more preferred one may be methyl and ethyl.

Suitable "acyl" in the term "acyl(lower)alkyl" may include lower alkanoyl (e.g. formyl, acetyl, propionyl, butyryl, isobutyryl, pivaloyl, hexanoyl, etc); carboxy; protected carboxy; and the like.

Suitable "protected carboxy" may be an esterified carboxy, amidated carboxy, or the like, in which concrete examples of esterified carboxy may be the ones such as lower alkoxycarbonyl (e.g. methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, 1-cyclopropylethoxycarbonyl, etc) which may have suitable substituent(s), for example, lower alkanoyloxy(lower)alkoxycarbonyl [e.g. acetoxymethoxycarbonyl, propionyloxymethoxycarbonyl, butyryloxymethoxycarbonyl, valeryloxymethoxycarbonyl, pivaloyloxymethoxycarbonyl, 1-acetoxyethoxycarbonyl, 1-propionyloxyethoxycarbonyl, pivaloyloxymethoxycarbonyl, 2-propionyloxyethoxycarbonyl, hexanoyloxymethoxycarbonyl, etc]; lower alkanesulfonyl(lower)alkoxycarbonyl [e.g. 2-mesylethoxycarbonyl, etc]; mono(or di or tri)-halo(lower)alkoxycarbonyl [e.g. 2-iodoethoxycarbonyl, 2,2,2-trichloroethoxycarbonyl, etc]; lower alkenyloxycarbonyl [e.g. vinyloxycarbonyl, allyloxycarbonyl, etc]; lower alkynyloxycarbonyl [e.g. ethynyloxycarbonyl, propynyloxycarbonyl, etc]; ar(lower)alkoxycarbonyl which may have suitable substituent(s) [e.g. benzyloxycarbonyl, 4-methoxybenzyloxycarbonyl, 4-nitrobenzyloxycarbonyl, phenethyloxycarbonyl, trityloxycarbonyl, benzhydryloxycarbonyl, bis(methoxyphenyl)methoxycarbonyl, 3,4-dimethoxybenzyloxycarbonyl, 4-hydroxy-3,5-di-t-butylbenzyloxycarbonyl, etc]; aryloxycarbonyl which may have suitable substituent(s) [e.g. phenoxycarbonyl, 4-chlorophenoxycarbonyl, tolyloxycarbonyl, 4-t-butylphenoxycarbonyl, xylyloxycarbonyl, mesityloxycarbonyl, cumenyloxycarbonyl, etc]; or the like, wherein the preferred one may be lower alkoxycarbonyl (e.g. methoxycarbonyl, ethoxycarbonyl, propoxycarbonyl, butoxycarbonyl, t-butoxycarbonyl, pentyloxycarbonyl, hexyloxycarbonyl, etc.), the more preferred one may be (C$_1$-C$_4$)alkoxycarbonyl and the most preferred one may be methoxycarbonyl; and concrete examples of amidated carboxy may be the ones such as carbamoyl; N-(lower)alkylcarbamoyl (e.g. N-methylcarbamoyl, N-ethylcarbamoyl, N-isopropylcarbamoyl, N-butylcarbamoyl, N-pentylcarbamoyl, N-hexylcarbamoyl, etc);

N-(higher)alkylcarbamoyl (e.g. N-heptylcarbamoyl, N-(2-methylheptyl)carbamoyl, N-nonylcarbamoyl, N-decanylcarbamoyl, N-tricyclo[3.3.1.1$^{3,7}$]decanylcarbamoyl, N-undecanylcarbamoyl, N-(bicyclo[4.3.2]-undecanyl)carbamoyl, N-dodecanylcarbamoyl, N-tridecanylcarbamoyl, N-tetradecanylcarbamoyl, N-pentadecanylcarbamoyl, N-hexadecanylcarbamoyl, N-heptadecanylcarbamoyl, N-octadecanylcarbamoyl, N-nonadecanylcarbamoyl, N-icosanylcarbamoyl, etc);

N,N-di(lower)alkylcarbamoyl [e.g. N,N-dimethylcarbamoyl, N,N-diethylcarbamoyl, N-methyl-N-ethylcarbamoyl, N,N-dipropylcarbamoyl, N,N-di(t-butyl)carbamoyl, N-pentyl-N-hexylcarbamoyl, etc];

N-lower alkyl-N-ar(lower)alkylcarbamoyl (e.g. N-methyl-N-benzylcarbamoyl, etc); or the like, wherein the preferred one may be carbamoyl, N-(lower)alkylcarbamoyl and N,N-di(lower)alkylcarbamoyl, the more preferred one may be carbamoyl, N-($C_1$-$C_4$)alkylcarbamoyl and N,N-di($C_1$-$C_4$)alkylcarbamoyl and the most preferred one may be carbamoyl, N-ethylcarbamoyl and N,N-diethylcarbamoyl.

In "acyl(lower)alkyl", the preferred one may be lower alkanoyl(lower)alkyl (e.g. formylmethyl, 1-formylethyl, 2-acetylethyl, 2-formylpropyl, 3-propionylpropyl, 4-formylbutyl, 2-butyrylbutyl, 1-(formylmethyl)ethyl, 3-formylpentyl, 1-isobutyrylpentyl, 4-pivaloylpentyl, 2-formylhexyl, 6-hexanoylhexyl, etc), carboxy(lower)alkyl (e.g. carboxymethyl, 1-carboxyethyl, 2-carboxypropyl, 1-(carboxymethyl)ethyl, 4-carboxybutyl, 3-carboxypentyl, 2-carboxyhexyl, etc) or protected carboxy(lower)alkyl, in which the more preferred "lower alkanoyl(lower)alkyl" may be ($C_1$-$C_4$)alkanoyl($C_1$-$C_4$)alkyl and the most preferred one may be formylmethyl;

the preferred "carboxy(lower)alkyl" may be carboxy($C_1$-$C_4$)alkyl and the most preferred one may be carboxymethyl;

and the preferred "protected carboxy(lower)alkyl" may be esterified carboxy(lower)alkyl and amidated carboxy(lower)alkyl, the more preferred one may be lower alkoxycarbonyl(lower)alkyl (e.g. methoxycarbonylmethyl, 2-methoxycarbonylethyl, 1-ethoxycarbonylethyl, 2-propoxycarbonylpropyl, 1-(methoxycarbonylmethyl)ethyl, 4-t-butoxycarbonylbutyl, 3-pentyloxycarbonylpentyl, 2-hexyloxycarbonylhexyl, etc), carbamoyl(lower)alkyl (e.g. carbamoylmethyl, 1-carbamoylethyl, 2-carbamoylethyl, 2-carbamoylpropyl, 1-(carbamoylmethyl)ethyl, 4-carbamoylbutyl, 3-carbamoylpentyl, 2-carbamoylhexyl, etc), N-(lower)alkylcarbamoyl(lower)alkyl [e.g. N-methylcarbamoylmethyl, N-ethylcarbamoylmethyl, 1-(N-ethylcarbamoyl)ethyl, 2-(N-ethylcarbamoyl)ethyl, 2-(N-isopropylcarbamoyl)propyl, 1-[(N-ethylcarbamoyl)methyl]ethyl, 4-(N-butylcarbamoyl)butyl, 3-(N-pentylcarbamoyl)pentyl, 2-(N-hexylcarbamoyl)hexyl, etc], N,N-di(lower alkylcarbamoyl(lower)alkyl [e.g. N,N-dimethylcarbamoylmethyl, N,N-diethylcarbamoylmethyl, 1-(N,N-dimethylcarbamoyl)ethyl, 2-(N,N-diethylcarbamoyl)-ethyl, 2-(N-methyl-N-ethylcarbamoyl)-propyl, 2-(N,N-dipropylcarbamoyl)propyl, 1-[(N,N-diethylcarbamoyl)methyl]ethyl, 4-(N,N-dibutylcarbamoyl)butyl, 3-(N,N-dipentylcarbamoyl)pentyl, 2-(N-pentyl-N-hexylcarbamoyl)hexyl, etc]; the much more preferred one may be ($C_1$-$C_4$)alkoxycarbonyl($C_1$-$C_4$)alkyl, carbamoyl($C_1$-$C_4$)alkyl, N-($C_1$-$C_4$)alkylcarbamoyl($C_1$-$C_4$)alkyl and N,N-di($C_1$-$C_4$)alkylcabamoyl($C_1$-$C_4$)alkyl, and the most preferred one may be methoxycarbonylmethyl, carbamoylmethyl, N-ethylcarbamoylmethyl, and N,N-diethylcarbamoylmethyl.

Suitable "hydroxy(lower)alkyl" may be the ones having 2 to 7 carbon atom(s) and having hydroxy at the terminal carbon atom such as 2-hydroxyethyl, 1-(hydroxymethyl)ethyl, 2-(hydroxymethyl)propyl, 1-(2-hydroxyethyl)ethyl, 5-hydroxypentyl, 3-(hydroxymethyl)pentyl, 2-carboxymethyl)hexyl, or the like, in which the preferred one may be hydroxy($C_2$-$C_5$)alkyl and the most preferred one may be 2-hydroxyethyl.

Suitable "formyl(lower)alkyl" may include formylmethyl, 1-formylethyl, 2-formylpropyl, 4-formylbutyl, 3-formylpentyl, 1-(formylmethyl)ethyl, 2-formylhexyl, and the like, in which the preferred one may be formyl($C_1$-$C_4$)alkyl and the most preferred one may be formylmethyl.

Suitable "lower alkenylene" may include vinylene, propenylene, 2-butenylene, 3-methyl-1-propenylene, 3-pentenylene, 1-hexenylene, and the like, in which the preferred one may be ($C_2$-$C_4$)alkenylene and the most preferred one may be vinylene.

The processes for preparing the object compound (I) of the present invention are explained in detail in the following.

PROCESS 1

The object compound (I) or a salt thereof can be prepared by reacting the compound (II) or its reactive derivative at the carboxy group or a salt thereof with the compound (III) or its reactive derivative at the amino group or a salt thereof.

Suitable salts of the compounds (II) and (III) can be referred to the ones as exemplified for the compound (I).

Suitable reactive derivative at the carboxy group of the compound (II) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc], dialkylphosphorus acid, sulfurous acid, thiosulfuric acid, sulfuric acid, sulfonic acid [e.g. methanesulfonic acid, etc], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc] or aromatic carboxylic acid [e.g. benzoic acid, etc]; a symmetrical acid anhydride; an activated amide with imidazole, 4-substituted imidazole, dimethylpyrazole, triazole, tetrazole or 1-hydroxy-1H-benzotriazole; or an activated ester [e.g. cyanomethyl ester, methoxymethyl ester, dimethyliminomethyl [($CH_3$)$_2$ =CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc] or an ester with a N-hydroxy compound [e.g. N,N-dimethylhydroxylamine, 1-hydroxy-2-(1 H)-pyridone, N-hydroxysuccinimide, N-hydroxyphthalimide, 1-hydroxy-1 H-benzotriazole, etc], and the like. These reactive derivatives can optionally be selected from them according to the kind of the compound (If) to be used.

Suitable reactive derivative at the amino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl)acetamide, bis(trimethylsilyl)urea or the like; a derivative formed by reaction of the compound (III) with phosphorus trichloride or phosgene, and the like.

The reaction is usually carried out in a conventional solvent such as water, alcohol [e.g. methanol, ethanol, etc], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; or the like.

The reaction may also be carried out in the presence of an inorganic or organic base such as an alkali metal carbonate, alkali metal bicarbonate, tri(lower)alkylamine (e.g. triethylamine, etc), pyridine, N-(lower)alkylmorpholine, N,N-di(lower)alkylbenzylamine, or the like.

The reaction temperature is not critical, and the reaction is usually carried out under cooling to warming.

PROCESS 2

The object compound (Ib) or a salt thereof can be prepared by subjecting the compound (Ia) or a salt thereof to elimination reaction of the carboxy protective group.

Suitable salt of the compound (Ia) can be referred to the acid addition salts as exemplified for the compound (I).

Suitable salt of the compound (Ib) can be referred to the ones as exemplified for the compound (I).

This reaction is carried out in accordance with a conventional method such as hydrolysis, or the like.

The hydrolysis is preferably carried out in the presence of a base or an acid including Lewis acid. Suitable base may include an inorganic base and an organic base such as an alkali metal [e.g. sodium, potassium, etc], an alkaline earth metal [e.g. magnesium, calcium, etc], the hydroxide or carbonate or bicarbonate thereof, trialkylamine [e.g. trimethylamine, triethylamine, etc], picoline, 1,5-diazabicyclo[4.3.0] non-5-ene, 1,4-diazabicyclo[2.2.2]octane, 1,8-diazabicyclo[5.4.0]-undec-7-ene, or the like.

Suitable acid may include an organic acid [e.g. formic acid, acetic acid, propionic acid, trichloroacetic acid, trifluoroacetic acid, etc] and an inorganic acid [e.g. hydrochloric acid, hydrobromic acid, sulfuric acid, hydrogen chloride, hydrogen bromide, etc]. The elimination using Lewis acid such as trihaloacetic acid [e.g. trichloroacetic acid, trifluoroacetic acid, etc] or the like is preferably carried out in the presence of cation trapping agents [e.g. anisole, phenol, etc].

The reaction is usually carried out in a solvent such as water, an alcohol [e.g. methanol, ethanol, etc], methylene chloride, tetrahydrofuran, a mixture thereof or any other solvent which does not adversely influence the reaction. A liquid base or acid can be also used as the solvent.

The reaction temperature is not critical and the reaction is usually carried out under cooling to heating.

PROCESS 3

The object compound (Ic) or a salt thereof can be prepared by. subjecting the compound (IV) or a salt thereof to oxidation reaction This oxidation reaction can be carried out by reacting the compound (IV) or a salt thereof with a conventional oxidizing agent to be used for the oxidation of hydroxy group in this field of the art.

Suitable examples of said oxidizing agent may be chromic acid; the Jones reagent; manganese dioxide; dimethyl sulfoxide activated by dicyclohexylcarbodiimide, acid anhydride (e.g acetic anhydride, etc) or acid halide (e.g. acetyl chloride, oxalyl dichloride, etc); or the like.

The reaction is usually carried out in a suitable solvent such as acetone, chloroform, methylene chloride, pyridine or any other solvent which does not adversely influence the reaction. The solvent is selected according to the reaction condition to be used.

The reaction temperature is not critical and the reaction is usually carried out under cooling, at room temperature or under warming.

PROCESS 4

The object compound (Id) or a salt thereof can be prepared by subjecting the compound (Ib) or its reactive derivative at the carboxy group or a salt thereof to amidation reaction.

This amidation reaction can be carried out by reacting the compound (Ib) or its reactive derivative at the carboxy group or a salt thereof with the amine compound to be introduced or its reactive derivative at the amino group or a salt thereof.

Suitable example of said amine compound may be a compound of the formula: [where $R_N$ is amino, N-lower alkylamino, N-higher alkylamino, N,N-di(lower)alkylamino or N-lower alkyl-N-ar(lower)alkylamino], or the like.

The reaction conditions of this process (e.g. salt, reactive derivative, solvent, reaction temperature, etc) can be referred to the ones as explained in aforesaid Process 1.

The object compound (I) of the present invention is an adenosine antagonist and possesses the various pharmaceutical actions as stated before In order to show this usefulness of the compound (I) of the present invention, the pharmacological test result of the representative compound of the present invention is shown in the following.

TEST 1

Diuretic Activity

[I] Test Method

Male JCL:SD strain rats aged 9 weeks and weighing 170–220 g were used after starving for 18 hours. Immediately after oral dosing with the test drug suspended in 0.5% methylcellulose (0.5% MC), the animals were given 20 ml/kg physiological saline orally. The rats were housed by threes in a metabolism cage. The urine was collected for 6 hours. Urine volume was measured with a volumetric cylinder.

[II] Test Compound (2R)-1-[3-(2-Phenylpyrazolo[1,5-a]pyridin-3-yl)-acryloyl]-2-(carboxymethyl)piperidine (trans isomer).

[III] Test Result

Excretion of Urine (control = 100).

| Dose (mg/kg) | Excretion (%) |
| --- | --- |
| 1 | 153 |

The pharmaceutical composition of this invention can be used in the form of a pharmaceutical preparation, for example, in solid, semisolid or liquid form, which contains the pyrazolopyridine compound (I) or a pharmaceutically acceptable salt thereof, as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation. The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used. The pyrazolopyridine compound (I) or a pharmaceutically acceptable salt thereof is/are included in the pharmaceutical composition in an amount sufficient to produce the desired aforesaid pharmaceutical effect upon the process or condition of diseases.

For applying the composition to human being or animals, it is preferable to apply it by intravenous, intramuscular, pulmonary, or oral administration, or insufflation. While the dosage of therapeutically effective amount of the pyrazolopyridine compound (I) varies from and also depends upon the age and condition of each individual patient to be treated, in the case of intravenous administration, a daily dose of 0.01–100 mg of the pyrazolopyridine compound (I) per kg weight of human being or animals, in the case of intramuscular administration, a daily dose of 0.1–100 mg of the pyrazolopyridine compound (I) per kg weight of human being or animals, in case of oral administration, a daily dose of 0.5–100 mg of the pyrazolopyridine compound (I) per kg weight of human being or animals in generally given for the prevention and/or treatment of aforesaid diseases.

The following Examples are given for the purpose of illustrating the present invention in more detail.

EXAMPLE 1

Thionyl chloride (145 mg) was added dropwise to a stirred mixture of 3-(2-phenylpyrazolo[1,5-a]pyridin-3-yl)acrylic acid (trans isomer) (270 mg) and N,N-dimethylformamide (1 drop) in methylene chloride (1.5 ml) under ice-cooling. After being stirred at room temperature for 2 hours and 50 minutes, the solvent was evaporated in vacuo to give acid chloride derivative. The above acid chloride derivative was added by portions to a stirred mixture of (R)-2-(methoxycarbonylmethyl)-piperidine hydrochloride (237 mg) and triethylamine (340 µl) in methylene chloride (1.5 ml) at −10° C.

The reaction mixture was stirred at room temperature overnight and then poured into ice-water (10 ml). The mixture was extracted with methylene chloride (20 ml × 2). The combined extracts were washed with 0.1 N HCl (10 ml), 10% aq $K_2CO_3$ (10 ml) and brine (10 ml), dried over sodium sulfate and evaporated in vacuo to give crude material, which was purified by column chromatography on silica gel (10 g) with a mixture of ethyl acetate and methylene chloride (1:10) as an eluent to give (2R)-1-[3-(2-phenylpyrazolo[1,5-a]pyridin-3-yl)acryloyl]-2-(methoxycarbonylmethyl)piperidine (trans isomer) (330 mg) as an oil.

$[\alpha]^{19}_D = +65.11°$ (C = 1.8, MeOH)

IR (Film): 1730, 1635, 1590, 1515 cm$^{-1}$

NMR [CDCl$_3$, δ): 1.33–1.77 (7 H, m), 2.61 (1 H, dd, J = 14.7 and 7.1 Hz), 2.76 (1 H, brd s), 3.66 (3 H, s), 4.76 (1 H, brd s), 6.90 (1 H, td, J = 6.9 and 1.2 Hz), 7.35 (1 H, t, J = 7.4 Hz), 7.43–7.55 (3 H, m), 7.72 (1 H, dd, J = 7.7 and 1.7 Hz), 7.95 (1 H, d, J = 15.5 Hz), 8.53 (1 H, d, J = 6.9 Hz)

MS: m/e 403 (M+)

EXAMPLE 2

(2RS)-1-[3-(2-Phenylpyrazolo[1,5-a]pyridin-3-yl)acryloyl]-2-(methoxycarbonylmethyl)piperidine (trans isomer) was obtained according to a similar manner to that of Example 1.

IR (Film): 1730, 1635, 1590, 1510 cm$^{-1}$

NMR spectrum was the same as that of the compound of Example 1.

EXAMPLE 3

A mixture of (2R)-1-[3-(2-phenylpyrazolo[1,5-a]-pyridin-3-yl)acryloyl]-2-(methoxycarbonylmethyl-)piperidine (trans isomer) (210 mg) and 1N sodium hydroxide solution (0.573 ml) in methanol (2.0 ml) was heated to reflux for 2 hours. Methanol was evaporated in vacuo and water (20 ml) was added to the residue. The solution was acidified with 1N hydrochloric acid and extracted with methylene chloride (10 ml × 2). The combined extracts were washed with brine (10 ml), dried over sodium sulfate and evaporated in vacuo. The crude crystals were recrystallized from a mixture of ethyl acetate and diethyl ether to give colorless crystals of (2R)-1-[3-(2-phenylpyrazolo[1,5-a]-pyridin-3-yl)acryloyl]-2-(carboxymethyl)piperidine (trans isomer) (152.7 mg).

mp: 165°–166° C.

$[\alpha]^{18}_D = +72.75°$ (C = 1.09, MeOH)

IR (Nujol): 1715, 1625, 1570, 1510 cm$^{-1}$

NMR (CDCl$_3$, δ): 1.36–1.82 (7 H, m), 2.57 (1 H, dd, J = 15.1 and 6.4 Hz), 2.67–3.25 (2 H, m), 4.69 (1 H, brd s), 6.40–7.34 (2 H, m), 7.37–7.51 (4 H, m), 7.65–7.77 (3 H, m), 7.89 (1 H, d, J = 15.5 Hz), 8.44 (1 H, brd s), 10.40 (1 H, brd s)

Analysis Calcd. for $C_{23}H_{23}N_3O_3$: C 70.93, H 5.95, N 10.79; Found: C 70.81, H 5.97, N 10.66.

EXAMPLE 4

(2RS)-1-[3-(2-Phenylpyrazolo[1,5-a]pyridin-3-yl)acryloyl]-2-(carboxymethyl)piperidine (trans isomer) was obtained according to a similar manner to that of Example 3.

mp: 132°–134° C.

IR (Nujol) 1705, 1625, 1560, 1505 cm$^{-1}$

NMR spectrum was the same as that of the compound of Example 3.

EXAMPLE 5

A solution of dimethyl sulfoxide (202 mg) in methylene chloride (1.0 ml) was added dropwise to a solution of oxalyl dichloride (247 mg) in methylene chloride (10 ml) over 5 minutes at $-78°$ C. After 10 minutes, a solution of (2R)-1-[3-(2-phenylpyrazolo[1,5-a]pyridin-3-yl)acryloyl]-2-(2-hydroxyethyl)piperidine (trans isomer) [364 mg] in methylene chloride (3.4 mg) was added dropwise over 10 minutes at $-78°$ C. The solution was stirred at $-78°$ C. for 20 minutes and at $-45°$ C. for 1 hour. Triethylamine (986 μl) was added to the solution and the mixture was stirred at $-20°$–$0°$ C. for 20 minutes Saturated ammonium chloride solution (20 ml) was added to the reaction mixture and the mixture was extracted with methylene chloride (10 ml×2). The combined extracts were washed with brine (10 ml), dried over magnesium sulfate and evaporated in vacuo. The crude material was purified by column chromatography on silica gel (10 g) with a mixture of methylene chloride and ethyl acetate (10:1) as an eluent to give (2R)-1-[3-(2-phenylpyrazolo-[1,5-a]pyridin-3-yl)acryloyl]-2-(formylmethyl)piperidine (trans isomer) (139.0 mg) as an oil.

$[\alpha]^{17}_D = +35.41°$ (C=1.44, MeOH)

IR (Film): 1720, 1640, 1590, 1520 cm$^{-1}$

NMR (CDCl$_3$, δ): 1.05–2.10 (8 H, m), 2.22–3.12 (3 H, m), 6.50–6.93 (2 H, m), 7.05–7.54 (4 H, m), 7.67–7.81 (3 H, m), 7.93 (1 H, d, J=15.4 Hz), 8.45–8.53 (1 H, m), 9.68–9.75 (1 H, m)

EXAMPLE 6

Thionyl chloride (0.2 ml) was added dropwise to a solution of methylene chloride (dry, 40 ml) and N,N-dimethylformamide (0.2 ml) at 0° C. and stirred for 30 minutes. To this cooled solution was added (2R)-1-[3-(2-phenylpyrazolo[1,5-a]pyridin-3-yl)acryloyl]-2-(carboxymethyl)piperidine (trans isomer) (1.0 g) and the mixture was stirred for 1.5 hours. To this solution was added a solution of 28% aqueous ammonia solution (20 ml) and stirring was continued for further 2 hours. The aqueous and organic phases were separated and the organic layer was evaporated. The oily residue was subjected to column chromatography (silica gel, 60 mesh) using ethyl acetate as eluent. Evaporation of the solvent afforded (2R)-1-[3-(2-phenylpyrazolo[1,5-a]pyridin-3-yl)acryloyl]-2-(carbamoylmethyl)piperidine (trans isomer) (405 mg) as a white granular solid.

mp: 195°–197° C.

IR (Nujol): 3440, 3160, 1675, 1645 cm$^{-1}$

NMR (CDCl$_3$, δ): 1.6–1.7 (7 H, m), 2.47 (1 H, dd, J=5.1 and J=15.9 Hz), 2.7 (1 H, brd d), 3.15 (0.25 H, brd t), 3.75 (0.3 H, brd s), 5.31 (1 H, brd d), 6.69 (0.5 H, d, J=15.43 Hz), 6.92 (1 H, t, J=5 63 Hz), 7.5 (5 H, m), 7.68 (2 H, dd, J=1.87 and J=7.6 Hz), 7.94 (1 H, d, J=15.43 Hz), 8.53 (1 H, d, J=6.9 Hz)

MS: m/e 388 (M+), 329, 247, 219, 218, 217, 141

Analysis Calcd. for C$_{23}$H$_{24}$N$_4$O$_2$388.468: C 71.1, H 6.2, N 14.4; Found: C 70.6, H 6.4, N 14.3.

The following compounds (Examples 7 and 8) were ned according to a similar manner to that of Example 6.

EXAMPLE 7

(2R)-1-[3-(2-Phenylpyrazolo[1,5-a]pyridin-3-yl)yloyl]-2-(N-ethylcarbamoylmethyl)piperidine (trans isomer)

mp: 142°–143° C.

IR (Nujol): 3500, 3450, 3300, 1655, 1640 cm$^{-1}$

NMR (CDCl$_3$, δ): 1.09 (3 H, t, J=7.27 Hz), 1.5 (1 H, brd s), 1.64 (1 H, s), 1.7 (6 H, m), 2.45 (1 H, dd, J=5.0 and J=15.17 Hz), 2.75 (0.6 H, brd s), 3.25 (2 H, m), 4.76 (0.25 H, brd d), 5.15 (0.25 H, brd d), 6.66 (0.3 H, d, J=15.3 Hz), 6.91 (1 H, t, J=6.25 Hz), 7.28–7.68 (8 H, m), 7.8 (1 H, d, J=15.30 Hz), 8.52 (1 H, d, J=6.91 Hz)

MS: m/e 416 (M+), 329, 245, 219, 169

Analysis Calcd. for C$_{25}$H$_{28}$N$_4$O$_2$·½H$_2$O: C 70.56, H 6.87, N 13.16; Found: C 70.23, H 6.99, N 13.03.

EXAMPLE 8

(2R)-1-[3-(2-Phenylpyrazolo[1,5-a]pyridin-3-yl)-acryloyl]-2-(N,N-diethylcarbamoylmethyl)piperidine (trans isomer)

IR (CHCl$_3$): 3700, 3500, 1643, 1600 cm$^{-1}$

NMR (CDCl$_3$, δ): 1.08 (3H, t, J=7.1 Hz), 1.18 (3H, t, J=7.1 Hz), 1.72 (7H, m), 2.6 (2 H, m), 3.33 (4 H, m), 5.10 (1 H, brd s), 6.90 (1 H, t, J=5.58 Hz), 7.46 (4 H, m), 7.69 (2 H, dd, J=6.23 and 7.7 Hz), 7.91 (1 H, d, J=15.3 Hz), 8.2 (0.25 H, brd s), 8.52 (1 H, d, J=6.92 Hz)

MS: m/e 44 (M+), 325, 247, 219, 197

EXAMPLE 9

A solution of (2R)-1-[3-(2-phenylpyrazolo[1,5-a]-pyridin-3-yl)acryloyl]-2-(carboxymethyl)piperidine (trans isomer) (5.73 g) in methanol (287 ml) was irradiated with sunlight for 32 hours. The yellow crystals were separated by filtration, washed with methanol, and dried under vacuum to give 4.97 g of its cis isomer. A suspension of this cis isomer (4.88 g) in methanol (350 ml) was heated to reflux and cooled to room temperature. The precipitates were collected by filtration, washed with methanol, and dried under vacuum to give yellow prisms of (2R)-1-[3-(2-phenylpyrazolo[1,5-a]pyridin-3-yl)acryloyl]-2-(carboxymethylpiperidine (cis isomer) (4.20 g).

mp: 195°–196° C.

IR (Nujol): 1715, 1625, 1570, 1525 cm$^{-1}$

NMR (DMSO-d$_6$, δ): 0.40–1.60 (6 H, m), 2.07 (0.5 H, dd, J=15.1 and J=5.1 Hz), 2.90 (0.5 H, t, J=12.5 Hz), 3.34 (1 H, brd s), 3.74 (0.5 H, brd d, J=13.3 Hz), 4.23 (0.5 H, brd d, J=13.3 Hz), 4.42–4.59 (0.5 H, m), 4.70–4.90 (0.5 H, m), 6.20 (0.5 H, d, J=12.0 Hz), 6.22 (0.5 H, d, J=12.0 Hz), 6.75 (0.5 Hz, d, J=12.0 Hz), 6.81 (0.5 H, d, J=12.0 Hz), 6.97 (1 H, t, J=6.6 Hz), 7.31 (1 H, t, J=7.9 Hz), 7.41–7.55 (4 H, m), 7.76–7.79 (2 H, m), 8.74 (1 H, d, J=6.9 Hz), 12.29 (1 H, brd s)

Analysis Calcd. for C$_{23}$H$_{23}$N$_3$O$_3$: C 70.93, H 5.95, N 10.79; Found: C 70.74, H 6.05, N 10.76.

The following compounds (Examples 10 to 16) were obtained according to a similar manner to that of Example 1.

EXAMPLE 10

(2R)-1-[3-(2-Phenylpyrazolo[1,5-a]pyridin-3-yl)-acryloyl]-2-(carboxymethyl)piperidine (trans isomer)

mp: 165°–166° C.

$[\alpha]^{18}_d = +72.75°$ (C=1.09, MeOH)

IR (Nujol): 1715, 1625, 1570, 1510 cm$^{-1}$

EXAMPLE 11

(2RS)-1-[3-(2-Phenylpyrazolo[1,5-a]pyridin-3-yl)-acryloyl]-2-(carboxymethyl)piperidine (trans isomer)

mp: 132°–134° C.

IR (Nujol): 1705, 1625, 1560, 1505 cm$^{-1}$

EXAMPLE 12

(2R)-1-[3-(2-Phenylpyrazolo[1,5-a]pyridin-3-yl)-acryloyl]-2-(formylmethyl)piperidine (trans isomer)
[α]$^{17}_d$= +35.41° (C=1.44, MeOH)
IR (Film): 1720, 1640, 1590, 1520 cm$^{-1}$

EXAMPLE 13

(2R)-1-[3-(2-Phenylpyrazolo[1,5-a]pyridin-3-yl)acryloyl]-2-(carbamoylmethyl)piperidine (trans isomer)
mp: 195°-197° C.
IR (Nujol): 3440, 3160, 1675, 1645 cm$^{-1}$

EXAMPLE 14

(2R)-1-[3-(2-Phenylpyrazolo[1,5-a]pyridin-3-yl)-acryloyl]-2-(N-ethylcarbamoylmethyl)piperidine (trans isomer)
mp: 142°-143° c.
IR (Nujol): 3500, 3450, 3300, 1655, 1640 cm$^{-1}$

EXAMPLE 15

(2R)-1-[3-(2-Phenylpyrazolo[1,5-a]pyridin-3-yl)-acryloyl]-2-(N,N-diethylcarbamoylmethyl)piperidine (trans isomer)
IR (CHCl$_3$): 3700, 3500, 1643, 1600 cm$^{-1}$

EXAMPLE 16

(2R)-1-[3-(2-Phenylpyrazolo[1,5-a]pyridin-3-yl)-acryloyl]-2-(carboxymethyl)piperidine (cis isomer)
mp: 195°-196° C.
IR (Nujol): 1715, 1625, 1570, 1525 cm$^{-1}$

What we claim is:

1. A pyrazolopyridine compound of the formula:

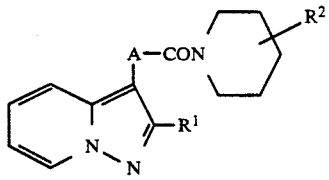

wherein
R$^1$ is aryl,
R$^2$ is acyl(lower)alkyl, carboxy(lower)alkyl or protected carboxy(lower)alkyl and
A is lower alkenylene,
or a pharmaceutically acceptable salt thereof.

2. A compound of claim 1, wherein
R$^1$ is phenyl, and
R$^2$ is lower alkanoyl(lower)alkyl, carboxy(lower)alkyl or protected carboxy(lower)alkyl.

3. A compound of claim 2, wherein
R$^2$ is lower alkanoyl(lower)alkyl, carboxy(lower)alkyl or protected carboxy(lower)alkyl,
wherein said protected carboxy(lower)alkyl group is (1) an esterified carboxy(lower)alkyl group wherein the esterified carboxy portion is selected form the group consisting of lower alkoxycarbonyl, substituted lower alkoxycarbonyl selected form the group consisting of lower alkanoyloxy(lower)alkoxycarbonyl, lower alkanesulfonyl(lower)alkoxycarbonyl, monohalo(lower)alkoxycarbonyl, dihalo(lower)alkoxycarbonyl, and trihalo(lower)alkoxycarbonyl, lower alkenyloxycarbonyl, lower alkynyloxycarbonyl, aryl(lower)alkoxycarbonyl, substituted aryl(lower)alkoxycarbonyl selected from the group consisting of 4-methoxybenzyloxycarbonyl, 4-nitrobenzyloxycarbonyl, phenethyloxycarbonyl, trityloxycarbonyl, benzhydryloxycarbonyl, bis(methoxyphenyl)methoxycarbonyl, 3,4-dimethoxybenzyloxycarbonyl, 4-hydroxy-3,5-di-t-butylbenzyloxycarbonyl, aryloxycarbonyl, and substituted aryloxycarbonyl selected from the group consisting of 4-chlorophenoxycarbonyl, tolyloxycarbonyl, 4-t-butylphenoxycarbonyl, xylyloxycarbonyl, mesityloxycarbonyl, and cumenyloxycarbonyl; or (2)an amidated carboxy(lower)alkyl group wherein the amidated carboxy portion is selected from the group consisting of carbamoyl, N-(lower)alkylcarbamoyl, N-(higher)alkylcarbamoyl, N,N-di(lower)alkylcarbamoyl, and N-lower alkyl-N-aryl(lower)alkylcarbamoyl.

4. A compound of claim 2, wherein
R$^2$ is lower alkanoyl(lower)alkyl, carboxy(lower)alkyl, esterified carboxy(lower)alkyl or amidated carboxy(lower)alkyl.

5. A compound of claim 4, wherein
R$^2$ is lower alkanoyl(lower)alkyl, carboxy(lower)alkyl, esterified carboxy(lower)alkyl, or amidated carboxy(lower)alkyl, wherein the esterified carboxy portion is selected form the group consisting of lower alkoxycarbonyl, substituted lower alkoxycarbonyl selected from the group consisting of lower alkanoyloxy(lower)alkoxycarbonyl, lower alkanesulfonyl(lower)alkoxycarbonyl, monohalo(lower)alkoxycarbonyl, dihalo(lower)alkoxycarbonyl, and trihalo(lower)alkoxycarbonyl, lower alkenyloxycarbonyl, lower alkynyloxycarbonyl, aryl(lower)alkoxycarbonyl, substituted aryl(lower)alkoxycarbonyl selected form the group consisting of 4-methoxybenzyloxycarbonyl, 4-nitrobenzyloxycarbonyl, phenethyloxycarbonyl, trityloxycarbonyl, benzhydryloxycarbonyl, bis(methoxyphenyl)methoxycarbonyl, 3,4-dimethoxybenzyloxy-carbonyl, 4-hydroxy-3,5-di-t-butylbenzyloxycarbonyl, aryloxycarbonyl, and substituted aryloxycarbonyl selected from the group consisting of 4-chlorophenoxycarbonyl, tolyloxycarbonyl, 4-t-butylphenoxycarbonyl, xylyloxycarbonyl, mesityloxycarbonyl, and cumenyloxycarbonyl; and the amidated carboxy portion is selected from the group consisting of carbamoyl, N-(lower)alkylcarbamoyl, N-(higher)alkylcarbamoyl, N,N-di(lower)alkylcarbamoyl, and N-lower alkyl-N-aryl(lower)alkylcarbamoyl.

6. A compound of claim 5, wherein
R$^2$ is lower alkanoyl(lower)alkyl, carboxy(lower)alkyl, lower alkoxycarbonyl(lower)alkyl, carbamoyl(lower)alkyl, N-lower alkylcarbamoyl(lower)alkyl or N,N-di(lower)alkylcarbamoyl(lower)alkyl.

7. A compound of claim 6, wherein R$^2$ is carboxy(lower)alkyl.

8. A compound of claim 7, which is 1-[3-(2-phenylpyrazolo[1,5-a]pyridin-3-yl)-acryloyl]-2-(carboxymethyl)piperidine.

9. A compound of claim 8, which is (2R)-1-[3-(2-phenylpyrazolo[1,5-a]pyridin-3-yl)-acryloyl]-2-(carboxymethyl)piperidine (trans isomer).

10. A pharmaceutical composition which comprises, as an active ingredient, a compound of claim 1, or a pharmaceutically acceptable salt thereof in admixture with a pharmaceutically acceptable carrier or excipient.

11. A method for the treatment of melancholia, heart failure, hypertension, renal insufficiency, renal toxicity, nephrosis, nephritis, edema, obesity, bronchial asthma, gout, hyperuricemia, sudden infant death syndrome, immunosuppression, diabetes, myocardial infarction, thrombosis, obstruction, arteriosclerosis obliterans, thrombophlebitis, cerebral infarction, transient ischemic attack or angine pectoris, which comprises administering an effective amount of a compound of claim 1 or a pharmaceutically acceptable salt hereof to human being or animals.

* * * * *